United States Patent [19]

Brady et al.

[11] Patent Number: 4,691,052

[45] Date of Patent: Sep. 1, 1987

[54] PROCESS FOR THE PREPARATION OF PYRETHROID ACIDS

[75] Inventors: William T. Brady, Sanger; Scott J. Norton, Argyle; Jinrea Ko, Denton, all of Tex.

[73] Assignee: S.C. Johnson & Son, Inc., Racine, Wis.

[21] Appl. No.: 871,153

[22] Filed: May 30, 1986

Related U.S. Application Data

[63] Continuation of Ser. No. 560,449, Dec. 12, 1983, abandoned.

[51] Int. Cl.$^4$ .............................................. C07C 51/00
[52] U.S. Cl. ..................... 562/506; 562/500; 568/348; 568/364; 568/381
[58] Field of Search ................ 562/506, 500; 568/348, 568/364

[56] References Cited

U.S. PATENT DOCUMENTS

| 4,028,418 | 6/1977 | Brink | 568/364 |
|---|---|---|---|
| 4,064,174 | 12/1977 | Verbrugge | 560/124 |
| 4,242,278 | 12/1980 | Martin | 568/364 |
| 4,284,821 | 8/1981 | Martin | 568/364 |
| 4,291,176 | 9/1981 | Heine | 560/9 |
| 4,390,719 | 6/1983 | Schwarze | 562/506 |

FOREIGN PATENT DOCUMENTS 2918468 11/1980 Fed. Rep. of Germany ...... 568/348

OTHER PUBLICATIONS

Krepski, J. Org. Chem., 43, pp. 2879–2882 (1978).
Bak, J. Org. Chem, 44, pp. 107–110 (1979).
Elliott, Chem. Soc. Rev., 7, pp. 473–475 (1978).

Primary Examiner—Michael L. Shippen
Attorney, Agent, or Firm—Fitzpatrick, Cella, Harper & Scinto

[57] ABSTRACT

Pyrethroid acids are prepared by conducting a cycloaddition reaction of a conjugated diene and a dihaloketene to form a dihalo-vinylcyclobutanone product; reducing the dihalo-vinylcyclobutanone product to a monohalo-vinylcyclobutanone product and then conducting a ring contraction with a base to form the desired acid product.

3 Claims, No Drawings

PROCESS FOR THE PREPARATION OF PYRETHROID ACIDS

This application is a continuation of application Ser. No. 560,449, filed Dec. 12, 1983, now abandoned.

BACKGROUND OF INVENTION

1. Field of the Invention

The invention relates to a process for preparing pyrethroid acids from conjugated dienes. In particular, it relates to a processs for producing chrysanthemic acid and its analogs in high yields.

2. Description of the Prior Art

Chrysanthemic acid and its analogs known generically as pyrethroid acids, have long been acknowledged as the effective components of pyrethroid esters, which esters are potent insecticides. It has been proposed in U.S. Pat. No. 4,028,418 to synthesize mixtures of cis- and trans-chrysanthemummonocarboxylic acid and derivatives and other substituted cyclopropanecarboxylic acids by essentially a two step process. In the first step a conjugated diene or the like is reacted with a monohaloketene, which is formed in situ, to produce a mixture of two different stereoisomers of a monohalo-cyclobutanone.

For example, 2,5-dimethyl-2,4-hexadiene is said to react stereospecifically with monochloroketene to give trans-2-chloro-4,4-dimethyl-3-(2'-methyl-1'-propenyl)-cyclobutanone and trans-2-chloro-3,3-dimethyl-4-(2'-methyl-1'-propenyl)cyclobutanone. The 2-halo-3,3-dimethyl-and 2-halo-4,4-dimethyl-cyclobutanones, after isolation and purification, are said to be subjected to a ring-contraction step, a Favorskii reaction, by heating them in the presence of a base. The resulting products are a mixture of salts of cis-and trans-chrysanthemum-monocarboxylic acid (2,2-dimethyl-3-isobutenylcyclopropane carboxylic acid). The overall yield for that reaction is said to be 42% for the first step and 25% for the second step, thus providing a total yield (0.42×0.25) of only 10.5% of theoretical.

The cycloaddition of dichloroketene with 2,5-dimethyl-2,4-hexadiene which provided two regioisomers, the beta-vinyl isomer,2,2-dichloro-4,4-dimethyl-3-(2-methylpropenyl)-cyclobutanone and a minor amount of the alpha-vinyl isomer, 2,2-dichloro-3,3-dimethyl-4-(2-methylpropenyl)cyclobutanone, was reported in *J. Org. Chem.*, Vol. 44, No. 1, p. 107–110, (1979). Attempts to reduce certain 2,2-dichlorocyclobutanones disclosed therein with dehalogenating agents, however, yielded primarily dehalo-cyclobutanones and only small yields of monohalo-cyclobutanones.

It has also been reported that certain mono-olefins can provide better yields of dichlorocyclobutanones, when phosphorous oxychloride is added to a reaction mixture containing such a mono olefin and in which dichloroketene is generated therein in situ, *J. Org. Chem.*, Vol. 43, No. 14, p. 2879–2882.

SUMMARY OF THE INVENTION

The present invention includes a process for preparing pyrethroid acids comprising:

(a) forming a dihalo-vinylcyclobutanone addition product from the reaction of a conjugated diene and a dihaloketene, optionally in the presence of phosphoryl chloride;

(b) reaction said dihalo-vinylcyclobutanone addition product with up to one equivalent of a dehalogenating reducing agent to reduce said addition product to its corresponding monohalo-vinylcyclobutanone product; and (c) reacting said monohalo-vinylcyclobutanone product with a base for inducing ring contraction to form a corresponding pyrethroid acid product.

It has been found that high yields of pyrethroid acids can be obtained from the present reaction sequence. When a dihaloketene is reacted with a conjugated diene of the invention and, optionally phosphoryl chloride, high yields of the two regioisomers of the resulting dihalo vinylcyclobutanones are obtained.

The dihalo products are then subjected to a selective reductive removal of only one halogen atom by treatment with one equivalent of a dehalogenating reducing agent of the invention to provide high yields of the corresponding monohalo-vinylcyclobutanone product. Tha selective reduction step is not regiospecific and yields two stereomers of each of the two isomeric dihalo-cycloadducts.

The four monohalo reduction products are then reacted with a suitable base to initiate a Favorskii-type ring contraction which is a regiospecific reaction, and yields a cis-and trans-pyrethroid acid product in high yields.

BEST MODE FOR CARRYING OUT THE INVENTION

The preferred conjugated dienes of the invention have the general formula A:

$R_1R_2C=CHCH=CR_3R_4$  Formula A in which $R_1$ and $R_2$ are each hydrogen, lower alkyl, preferably $C_1$-$C_3$ alkyl, lower carboxy, lower alkoxyalkyl or, together, are cycloalkyl and $R_3$ and $R_4$ are each lower alkyl or together are spiro —$(CH_2)_n$—, where $n=2$-$6$. The conjugated diene is reacted to form a dihalo cycloaddition product, which in turn is reduced to its monohalo form and then ring contracted to form a pyrethroid acid of the formula B:

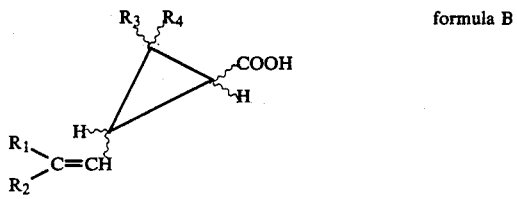

formula B

More preferred conjugated dienes are those having formula I as follows:

$RRC=CHCH=C(CH_3)_2$  formula I wherein R is $CH_3$ or H.

Another type of preferred conjugated diene is that formed from a conjugated vinylcycloalkene and a vinylcyclodiene, such as 6,6-dimethyl-fulvene.

The first step in the process of the invention is the cycloaddition of a dihaloketene, preferably dichloroketene, to a conjugated diene of the invention. Dicholoroketene is formed, in situ, by well known techniques employing acetyl halides. For example, the ketene may be generated by the dehydrohalogenation of a dichloroacetylhalide with an amine, such a triethylamine. Other acetyl chlorides may also be employed for forming the dichloroketene, such as 2,2-dichloropropanoyl chloride, dichloromonocyclohexyl chloride, dichloromonophenylacetyl chloride and the like. More preferably, the dihaloketene is formed by the dehalogenation of trichloroacetyl bromide or trichloroacetyl chloride or the like in the presence of a dehalogenating metal such as zinc, tin, magnesium or the like.

The cycloaddition should be carried out in an inert aprotic polar solvent to prevent side reactions. Typical solvents include, for example, tetrahydrofuran, ethyl acetate, ketones and, preferably, ethers, or mixtures thereof.

Even under the best conditions, however, yields of the desired dichlorocyclobutanones can be low. To improve yields, it has proven useful to employ phosphorous oxychloride (also known as phosphoryl chloride) in the reaction mix.

In general, the molar proportion of dehalogenating metal, acid halide and conjugated diene in this step is about 1:1:1-4. An excess of the diene is preferred to improve yields. Usually the phosphorous oxychloride is employed in stoichiometric amounts with both the zinc dehalogenating metal and acid halide. While preferred proportions of ingredients have been provided, it will be appreciated that weight proportions may be employed both above and below the recited proportions.

To initiate the reaction a solution of acid halide and phosphorous oxychloride predissolved in ether is added, with stirring, to a mixture of the conjugated diene and dehalogenating metal, preferably zinc, in ether solvent. The acid halide is added slowly over a period preferably from 30 minutes to 24 hours, with best results often obtained with an addition over at least several hours. Thereafter, the reaction mixture is stirred from about 30 minutes to 24 hours, preferably at least about 12 hours. to complete the reaction. Longer addition times are usually preferred in order to prevent local build-up of acetyl halide and a sudden initiation of the reaction which can lead to formation of undesired polymeric products.

The reaction temperature can range from ambient temperature to reflexing ether temperature. The dehalogenating metal, such as zinc, tin or magnesium is employed in an activated form, such as dust or small particle.

The dihalogenated vinylcyclobutanone addition product formed is recovered by removing the excess zinc or other dehalogenating metal by filtration; concentrating the resulting solution by distillation or the like; adding an inert hydrocarbyl solvent, such as pentane or cyclohexane, to extract the product and, thereafter, decanting the product-contaning solvent from the zinc halide etherate. The solvent solution is washed with a saturated salt solution, the solvent is vacuum distilled off and the residue, recovered. The yield of desired addition product is generally from 50-80% and, under most conditions, from 70-75% of theoretical, depending upon the particular diene selected.

The dihalogenated product will be either the cis- or trans-isomer depending on structure of the the diene employed. The product will be found as a mixture of alpha-vinyl dichlorocyclobutanone and the beta-vinyl stereoisomer, for example:

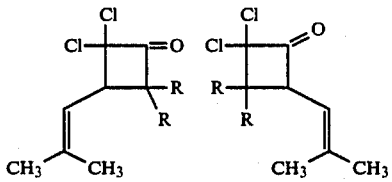

wherein R is as before.

In the second step of the process of the invention the dihalogenated vinylcyclobutanone is reduced to its corresponding monohalogenated product. It is critical to this step that only one halo atom be removed from the cyclobutanone ring. Accordingly, a reducing agent is employed in amounts sufficient to remove only one equivalent of halogen. If the dihalo product is completely dehalogenated and both halogen atoms are removed, then the ring contraction cannot be carried out by the Favorskii-type mechanism in the next step. Therefore, for the preferred dichlorovinylcyclobutanones of the invention only one equivalent of reducing agent is employed. The proportion of reducing agent to dihalogenated product is, therefore, 1:1.

The preferred reducing agents are dehalogenating ones including chromous chloride, tin-hydrochloric acid and tri-n-butyl tin hydride. The most preferred reducing agent is zinc dust with acetic acid.

In a preferred embodiment the dihalogenated vinylcyclobutanone product from step 1 is admixed with acetic acid and water and the resulting mixture slowly added to the zinc dust or other reducing agent. The addition is usually conducted over a period from 15 minutes to two hours, with a one hour addition time usually being sufficient. Thereafter, the reaction mixture is stirred for 24 hours to ensure completion of the reacton, although longer or shorter stirring times can be employed. The reaction temperature is usually ambient or room temperature, although somewhat higher temperatures can be employed, if needed.

The monohalovinylcyclobutanone reaction product is purified by extracting it with ether, washing with carbonate solution, drying the product and distilling off the solvent.

This step is not regiospecific and yields two stereomers for each regioisomer of the cycloadduct. Accordingly, if the dihalocycloadduct is found in the alpha and beta forms, then a cis- and trans-isomer pair is recovered for each such form. A preferred monochloro vinylcyclobutanone reaction product of this step is as follows:

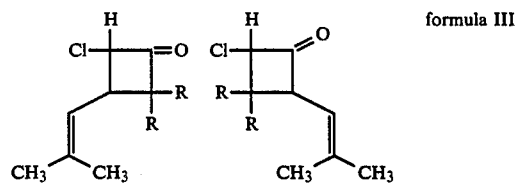

formula III

The typical yield of monohalo product for this step is between 80 and 100% of the theoretical and from 85-90% in most instances.

In the third step of the process, the monohalogenated product of step 2 is reacted with an appropriate aqueous solution of base to effect ring contraction and formation of the desired pyrethroid acid product. This step can be performed employing sodium hydroxide or any other common base, and preferably, potassium hydroxide. The proportion of base to monohalo reaction product is preferably at least 2 equivalents base to 1 equivalent reaction product. Best results are obtained when an excess of base is employed, although proportions 1:1 are permissible.

The reaction mixture is usually stirred slowly at room temperature for 24 hours to ensure completion. The resulting pyrethroid acid product may be produced in a liquid or solid form. If liquid, it may be purified, directly. If solid, it is often necessary to heat the reaction product at temperatures of 100° C. for several hours to ensure reaction completion.

Since the Favorskii ring contraction reaction is regiospecific, the four monohalocyclobutanones yield both cis- and trans-pyrethroid acids. The pyrethroid acid mixture is purified by washing with it with chloroform to remove unreacted product, the aqueous solution is acidified, extracted with chloroform to isolate the product, the product is dried, and any remaining solvent, distilled off. The residue, a mixture of cis-and trans-isomers of the desired acid is subjected to separation techniques commonly used to separate cis- and trans-isomers. The trans-form can be crystallized, for example, from ethyl acetate and the filtrate cooled to yield the cis- form. The typical yield of acid product is usually from 65 to 80% of theoretical.

When the preferred monochlorocyclobutanones of Formula III are reacted with a base, the isomeric chrysanthemic acids of formula IV are formed as follows:

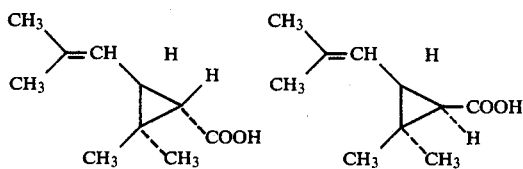

The overall yield of pyrethroid acid from the starting conjugated diene is typically from 30 to 65%, often from 40–50% of the theoretical, which is a far superior yield compared to that typically obtained by the prior art procedures using a monochloroketene synthesis to directly product a monochloro cycloaddition product.

The following Examples serve to illustrate a preferred embodiment of the invention.

EXAMPLE 1

In order to illustrate the results obtained by following the process of the invention the following three-step reaction sequence was conducted:

Step 1:

Preparation of
2,2-Dichloro-4,4-dimethyl-3-(2-methylpropenyl)-cyclobutanone (a) and
2,2-Dichloro-3,3-dimethyl-4-(2-methylpropenyl)-cyclobutanone, (b)

A solution of freshly distilled trichloroacetyl chloride (25 mmol) and phosphoryl chloride (25 mmol) in 250 ml of anhydrous ether was added over a 10 hour period to a stirred mixture of 2,5-dimethyl-2,4-hexadiene (0.1 mol) and 1.64 g activated zinc (25 mmol) in 250 ml ether at ambient temperature. After the addition was complete, the mixture was stirred for an addition 12 hours.

The excess zinc was removed by filtration and the solution concentrated to about 50 ml and then stirred with pentane (100 ml). The solution was decanted from the zinc chloride etherate and washed with water (200 ml) and a saturated solution of sodium hydrogen carbonate (100 ml). The pentane solvent was removed under reduced pressure and the residue vacuum distilled at 55–58%° C./0.2 torr to give title the product:

yield: 3.1 g (55% theoretical). The ratio of the beta-4,4 dimethyl product to the alpha-3,3-dimethyl product is 3:1.

Step 2:

Preparation of
2-Chloro-4,4-dimethyl-3-(2-methylpropenyl)-cyclobutanone, (c) and
2-Chloro-3,3-dimethyl-4-(2-methylpropenyl)-cyclobutanone, (d)

A mixture of 4.0 g (18 mmol) of (a) and (b), the title products of step 1, in 50 ml acetic acid and 5 ml water was added in portions to zinc dust (18 mmol) over a 1 hour period and then the mixture was stirred for 24 hours at ambient temperature. 150 ml of ether was added to the mixture and the mixture washed with 500 ml of water and 200 ml of sodium hydrogen carbonate solution. The ether solution was dried with anhydrous magnesium sulfate and the ether solvent removed under reduced pressure. The residue was vacuum distilled to give a mixture of (c) and (d); yield: 2.8 g (82%); b.p. 58°–60° C./0.1 torr.

Step 3:

Preparation of cis and trans-Chrysanthemic Acids

A 2 g mixture of the title products of Step 2 (c) and (d), were is treated with potassium hydroxide (2 equiv) in water (50 ml) at ambient temperature for 24 hours. The solution was then washed with chloroform (100 ml) to remove unreacted cyclobutanone and/or non-acidic products. The aqueous solution was then acidified with 2 normal hydrochloric acid and extracted with chloroform (200 ml), dried with anhydrous magnesium sulfate, and evaporated under reduced pressure. The residue was vacuum distilled to give cis- and trans-chrysanthemic acids; yield: 1.3 g (73%); b.p. 95°–96° C./0.25 torr or 138°–139° C./10 torr; trans/cis ratio-3.

The trans-acid was crystallized from ethyl acetate at −10° C. (2 days), washed with petroleum ether, and recrystallized from ethyl acetate, m.p. 54° C. The filtrate was cooled to −78° C. to yield the cis-acid; m.p. 115°–116° C. (the m.p. and H-N.M.R. data of cis- and trans-chrysanthemic acids are identical with those in the literature).

EXAMPLE 2

In order to further illustrate the process of the invention the procedure of Example 1 was repeated with the following exceptions:

Step 1:

Preparation
2,2,-Dichloro-3-(2-methylpropenyl)-cyclobutanone. (Product A)

The first step of Example 1 was repeated employing as the reactants, 5.6 ml trichloroacetyl chloride (50 mmol), 5 g (60 mmol) 4-methyl-1,3-pentadiene, 4.6 ml (50 mmol) phosphoryl chloride, 5 g (78 mmol) zinc and 500 ml ether. The yield was 6.8 g. or 71% theoretical, boiling at 65°-67° C. at 0.2 torr.

Step 2:
Preparation of 2-Chloro-3-(2 methylpropenyl)-cyclobutanone. (Product B)

Product A was added (as in Step 2 of Example 1) at 5 g (26 mmol) to 1.7 g zinc, 50 ml acetic acid and 5 ml water for 20 hours at ambient temperature. The yield was 3.2 g or 79% of the theoretical with the product boiling at 52°-54° C. at 0.1 torr. Both the endo and exo forms of Product B were identified by N.M.R. techniques.

Step 3:
Preparation 2-(2-methylpropenyl cyclopropanecarboxylic Acid. (Product C)

This step was performed in the same manner as Step 3 of Example 1 except that 2 g (12 mmol) of Product B, 1.6 g (30 mmol) potassium hydroxide and 50 ml water were employed at a 24 hour reacion time conducted at ambient temperature. The yield of Product C was 1.2 g or 75% of the theoretical, having a trans/cis ratio of 10:1.

$C_8H_{12}O_2$ (140.2). Calc: C 63.54, H 8.63. Found: C 68.23, H 8.69.

EXAMPLE 3

To illustrate another embodiment of the process of the invention the following reaction sequence was conducted:

Step 1:
Preparation of 7,7,-Dichloro-4-isopropylidenebicyclo[3.2.0]hept-2-en-6-one:

A solution of 13.8 g dichloroacetyl chloride (93 mmol) in hexane (10 ml) was added dropwise to a warm (40° C.) solution of 10 g of 6,6-dimethylfulvene (94 mmol) and 9.5 g triethylamine (94 mmol) in hexane (500 ml) during a 5 hour period. The amine salt was removed by filtration and the filtrate washed with water. The solvent was removed under reduced pressure and the residue vacuum distilled to give the desired 7,7-dichloro product; yield 18.2 g (89%) b.p. 94° C./0.25 torr.

Step 2:
Preparation of 7-Chloro-4-isopropylidene bicyclo[3.2.0.]hept-2-en-6-one 7,7-dichloro-4-isopropylidene bicyclo[3.2.0.]hept-2-en-6-one was reacted in accordance with the procedure of Step 2 of Example 1 with the exception that 10 g (46 mmol) of the title product of Step 1 herein, 3.0 g (46 mmol) zinc, 100 ml acetic acid and 10 ml water, were employed. The reaction was conducted for 24 hours at ambient temperature to yield 6.8 g or 82% of the theoretical yield of the desired product having a melting point of 63° C.

Step 3:
Preparation of 4-Isopropylidenebicyclo[3.1.0.]hex-2-en-6-carboxylic acid The title compound of Step 3 was prepared in accordance with the general procedure of Step 3 of Example 1 with the exception that 5 g (27 mmol) of the title compound of Step 2, 4.0 g (70 mmol) potassium hydroxide and 100 ml water were utilized and the reaction conducted for 24 hours at ambient temperature. The yield was 41 g or 68% of the theoretical of product having a m.p. 135°-137° C., as recrystallized from hexane/benzene.

What is claimed is:

1. Process for forming isomeric vinyl-substituted cyclopropanecarboxylic acids which comprises:
    (a) reacting a conjugated diene of Formula I as follows:

    $$RRC=CHCH=C(CH_3)_2 \qquad \text{Formula I}$$

wherein R is $CH_3$ or H; with dichloroketene in the presence of phosphoryl chloride to form a mixture of dichloro-vinylcyclobutanones of the Formula II as follows:

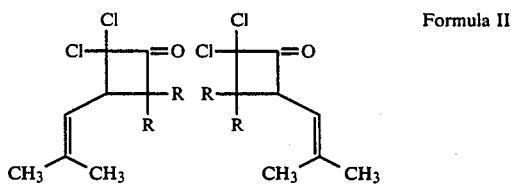

(b) reducing the dichlorovinylcyclobutanones of Formula II to a mixture of monochlorovinylcyclobutanones of Formula III as follows with one equivalent of a dehalogenating reducing agent, wherein the dehalogenating reducing agent is zinc dust and acetic acid:

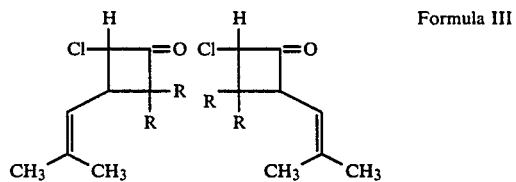

(c) reacting said mixture of monochlorovinylcyclobutanones of Formula III with a base to form isomeric vinyl-substituted cyclopropanecarboxylic acids of the Formula IV as follows:

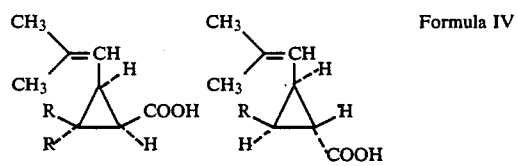

2. Process for preparing vinyl-substituted cyclopropanecarboxylic acids comprising:
    (a) forming a dihalo-vinylcyclobutanone addition product from the reaction of a dihaloketene and a conjugated diene of the Formula A in the presence of phosphoryl chloride, wherein the conjugated diene has the structure

    $$R_1R_2C=CHCH=CR_3R_4 \qquad \text{Formula A}$$

wherein $R_1$ $R_2$ are each hydrogen, lower alkyl, lower carboxy, lower akoxyalkyl or, together, are cycloalkyl and $R_3$ and $R_4$ are each lower alkyl or, together are spiro —$(CH_2)_n$, where n=2-6;

(b) reacting said dihalo-vinylcyclobutanone addition product with up to one equivalent of dehalogenating reducing agent to reduce said addition product to its corresponding monohalo-vinylcyclobutanone, wherein the dehalogenating reducing agent is zinc dust and acetic acid; and (c) reacting said monohalo-vinylcyclobutanone product with a base for inducing ring contraction to form a corresponding vinyl-substituted cyclopropanecarboxylic acid product of a structural Formula B:

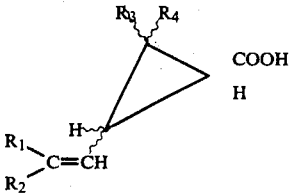

Formula B wherein, $R_1$ $R_2$ $R_3$ and $R_4$ are as before.

3. The process of claim 2 in which said dihaloketene is formed in situ in step (a) by dehalogenating an acid halide in the presence of a dehalogenating metal.

* * * * *

UNITED STATES PATENT AND TRADEMARK OFFICE
CERTIFICATE OF CORRECTION

PATENT NO. : 4,691,052

DATED : September 1, 1987

INVENTOR(S) : WILLIAM T. BRADY, ET AL.

Page 1 of 4

It is certified that error appears in the above-identified patent and that said Letters Patent is hereby corrected as shown below:

On the title page

AT [56] IN REFERENCES CITED

"Brink" should read --van den Brink et al.--.
"Martin" should read --Martin et al.--.
"Martin" should read --Martin et al.--.
"Heine" should read --Heine et al.--.
"Schwarze" should read --Schwarze et al.--.

COLUMN 1

Line 12, "chrysanthemic" should read --chrysanthemumic--.
Line 15, "Chrysanthemic" should read --Chrysanthemumic--.
Line 22, "two step" should read --two-step--.
Line 39, "to 42%" should read --to be 42%--.
Line 51, "dehalo-cyclobutanones" should read
    --dihalo-cyclobutanones--.
Line 67, "reaction" should read --reacting--.

COLUMN 2

Line 12, "dihalo vinylcyclobutanones" should read
    --dihalo-vinylcyclobutanones--.
Line 18, "Tha" should read --That--.
Line 64, "well known" should read --well-known--.

COLUMN 3

Line 56, "product-contaning" should read
    --product-containing--.
Line 65, "structure of the the" should read --the structure
    of the --.

UNITED STATES PATENT AND TRADEMARK OFFICE
CERTIFICATE OF CORRECTION

PATENT NO. : 4,691,052
DATED : September 1, 1987
INVENTOR(S) : WILLIAM T. BRADY, ET AL.

It is certified that error appears in the above-identified patent and that said Letters Patent is hereby corrected as shown below:

COLUMN 4

Line 37, "reacton," should read --reaction,--.

COLUMN 5

Line 30, "santhemic" should read --santhemumic--.
Line 32, insert --Formula IV--.
Lines 32-38,
"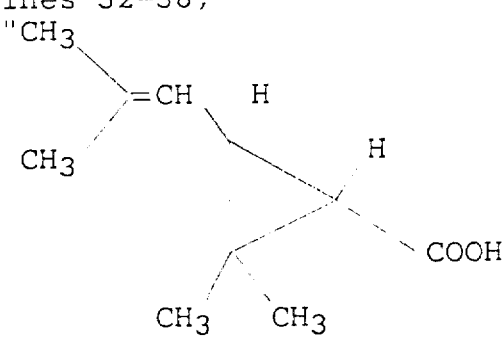 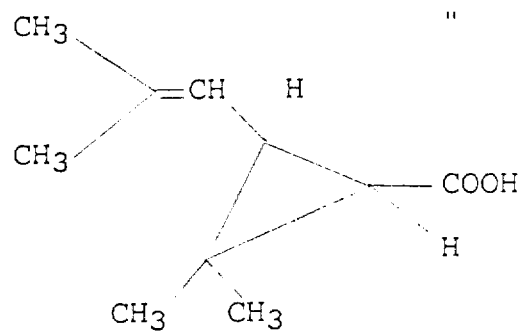"

should read
--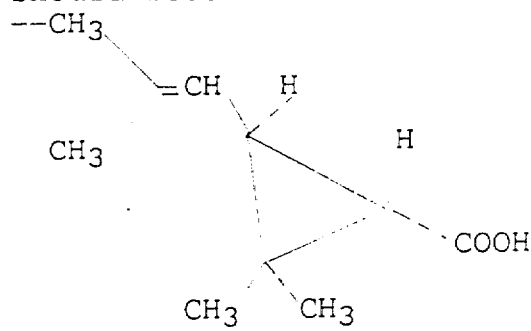 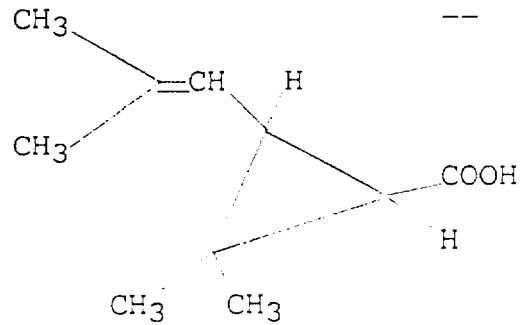--

UNITED STATES PATENT AND TRADEMARK OFFICE
CERTIFICATE OF CORRECTION

PATENT NO. : 4,691,052  Page 3 of 4
DATED : September 1, 1987
INVENTOR(S) : WILLIAM T. BRADY, ET AL.

It is certified that error appears in the above-identified patent and that said Letters Patent is hereby corrected as shown below:

COLUMN 5

Line 44, "product" should read --produce--.
Line 66, "addition" should read --additional--.

COLUMN 6

Line 7, close up left margin.
Line 32, "cis and" should read --cis- and--.
Line 32, "Chrysanthemic" should read --Chrysanthemumic--.
Line 35, delete "is".
Line 44, "chrysanthemic" should read --chrysanthemumic--.
Line 52, "chrysanthemic" should read --chrysanthemumic--.
Line 61, "Preparation" should read --Preparation of--.

COLUMN 7

Line 16, "Preparation 2-(2-methylpropenyl" should read
         --Preparation of 2-(2-methylpropenyl)--.
Line 21, "reacion" should read --reaction--.

COLUMN 8

Line 66, "akoxyalkyl" should read --alkoxyalkyl--.
Line 68, "spiro-$(CH_2)_n$," should read
         --spiro-$(CH_2)_n$- --.

UNITED STATES PATENT AND TRADEMARK OFFICE
CERTIFICATE OF CORRECTION

PATENT NO. : 4,691,052  
DATED : September 1, 1987  
INVENTOR(S) : WILLIAM T. BRADY, ET AL.

Page 4 of 4

It is certified that error appears in the above-identified patent and that said Letters Patent is hereby corrected as shown below:

COLUMN 10

Lines 1-9, " 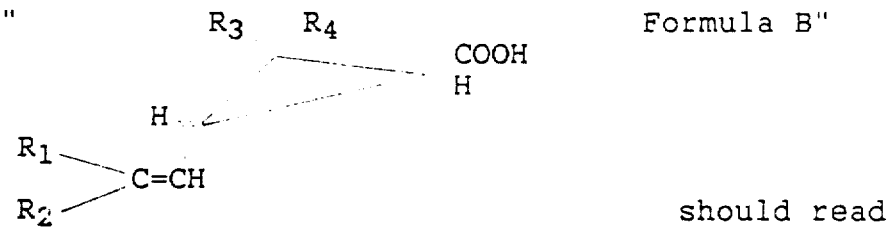 Formula B"

should read

-- 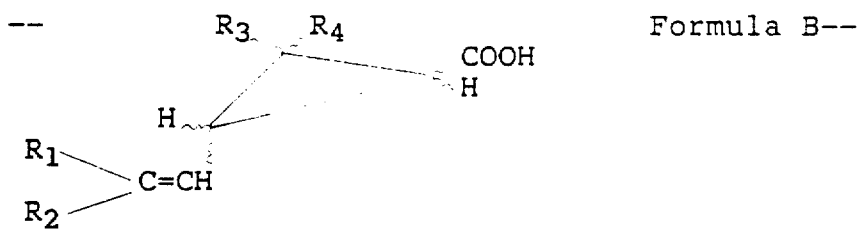 Formula B--

Signed and Sealed this

Twenty-ninth Day of March, 1988

Attest:

DONALD J. QUIGG

Attesting Officer  Commissioner of Patents and Trademarks